(12) United States Patent
Yokota et al.

(10) Patent No.: US 6,281,229 B1
(45) Date of Patent: Aug. 28, 2001

(54) HEAT SHOCK FACTOR ACTIVITY INHIBITORS

(75) Inventors: Shin-ichi Yokota, Takasago; Kozo Yamamoto, Ibaraki; Souichi Morikawa; Yoshihide Fuse, both of Himeji; Mikio Kitahara, Kobe, all of (JP)

(73) Assignee: Kaneka Corporation (JP)

( * ) Notice: Subject to any disclaimer, the term of this patent is extended or adjusted under 35 U.S.C. 154(b) by 0 days.

(21) Appl. No.: 09/446,286

(22) PCT Filed: Jun. 25, 1998

(86) PCT No.: PCT/JP98/02829

§ 371 Date: Dec. 21, 1999

§ 102(e) Date: Dec. 21, 1999

(87) PCT Pub. No.: WO99/00382

PCT Pub. Date: Jul. 1, 1999

(30) Foreign Application Priority Data

Jun. 27, 1997 (JP) .................................................. 9-171321

(51) Int. Cl.$^7$ ..................... A61K 31/445; A61K 31/40; C07D 405/06
(52) U.S. Cl. ..................... 514/321; 514/422; 546/197; 548/526
(58) Field of Search ..................... 546/197; 548/526; 514/321, 422

(56) References Cited

U.S. PATENT DOCUMENTS 5,270,339   12/1993   Yamamoto et al. .................. 514/408
5,607,953 * 3/1997   Minami et al. ....................... 514/327
5,618,835 * 4/1997   Wu et al. .............................. 514/422

FOREIGN PATENT DOCUMENTS

WO 92/17447   10/1992   (WO).

OTHER PUBLICATIONS

Akagawa et al. "Stresgenin B, an inhibitor of heat . . . " CA 132:90471, (1999).*
1998 PCT International Search Report.
1965 Zimmer, Hans et al., The Aldol Condensation of Aromatic Aldehydes with N–Acetyl–2–pyrrolidinone: Synthesis of 3–Arylidene–2–pyrrolidinones, Department of Chemistry, University of Cincinnati, Jun. 1965, pp. 171–175.

* cited by examiner

Primary Examiner—Ceila Chang
(74) Attorney, Agent, or Firm—Baker Botts L.L.P.

(57) ABSTRACT

A disease treatment is provided by controlling the expression of a protein induced by a heat shock factor.

The novel compound benzo-1,3-dioxole provides an inhibitor of HSF activity or an inhibitor of inducing the production of a protein regulated by HSF, which inhibits the activity of a heat shock factor, a transcriptional regulatory factor, thereby in turn inhibiting transcription of a structural gene having a heat shock element sequence in the gene region for transcriptional regulation into RNA, and thus inhibiting translation of the gene into a protein, and resulting in inhibition of inducing production of RNA or protein encoded by the gene. It also provides a drug for treating or preventing cancer through thermotherapy and a drug for treating or preventing stress diseases such as depression.

33 Claims, No Drawings

HEAT SHOCK FACTOR ACTIVITY INHIBITORS

TECHNICAL FIELD

The present invention relates to a heat shock factor (HSF) activity inhibitor, an expression suppressor for a substance encoded by a structural gene having a heat shock element (HSF) sequence in the gene region for transcriptional regulation, a treatment for or prevention of cancer based on the same, and a drug for treating or preventing stress diseases.

BACKGROUND ART

In order to produce a protein, a cell transcribes an mRNA from a DNA, i.e., a gene, and further translates the mRNA into the protein. It is clear that if the transcription is suppressed, the protein encoded by the DNA cannot be expressed. Transcription involves many factors called transcription factors. Transcription factors can be classified into basal transcription factors and transcription regulatory factors. While basal transcription factors are involved in most gene transcriptions, transcription regulatory factors are involved in transcriptions during a particular period or under particular conditions. HSF is one of such transcription regulatory factors, and is present in an evolutionarily wide range of species, from yeast to humans. HSF is characterized in that it specifically induces expression of a group of genes controlled thereby although transcription of protein synthesis in general is suppressed under environmental or physical stress such as heat or chemicals such as an amino acid analog, ethanol or a peroxide. It is known that upon activation HSF is turned from a monomer into a homotrimer in the cytoplasm and is transferred into the nucleus so as to recognize and bind to a binding sequence on a DNA called the HSE sequence (a base sequence of about 8 bp or more), thereby inducing and transcribing an mRNA (Mol. Cell. Biol., 13: 2486, 1993). Four types of HSF, HSF1 to HSF4, have been reported. It is believed that HSF1 is induced by external stress such as heat (Mol. Cell. Biol., 17: 468, 1997). Proteins which have the HSE sequence and are transcribed and translated from genes controlled by HSF are generically called heat shock proteins (HSPs), stress proteins, or chaperone proteins. Examples of HSPs, include, for example, HSP70, HSP90, HSP100, etc., and it has been reported that HSF actually functions in the expression of these HSPs. Conventionally, flavonoids such as quercetin are known as HSF inhibitors (Cell Struct. Func., 15: 393, 1990).

Stress includes cellular-level stress and animal-level stress, and the relationship between the cellular-level regulation/control of stress and the animal-level treatment of stress is an issue that should be studied. The present invention provides treatment of diseases by controlling the expression of a protein which is induced by stress, i.e., by HSF. Many HSPs are usually synthesized in a cell through a transcription mechanism other than the HSF activation. Some HSPs are believed to be essential for the cell to function properly (Nature, 355: 33, 1992; Nature, 381: 571, 1996). Generally, an inhibitor which provides its function by binding to a protein may, depending on the type of the target protein, affect cells or tissues which are not intended to be treated, thereby causing serious side effects. Since HSF is a stress-induced transcription factor, its inhibitor is believed to inhibit the transcription or the signal transmission during the HSF activation. By nature, HSF is activated to induce expression only when the cell is under a specific environment. The HSF inhibition as used herein aims to affect as little as possible the expression of the essential HSPs which are normally required by the cell while suppressing only the induction by stress, including abnormal induction. Heretofore, there has not been any drug which is capable of specifically suppressing only the induction under stress such as heat, and yet satisfactory in terms of the effectiveness, specificity, or the like.

The HSF activation process, i.e., the HSF modification and signal transmission caused by a stress stimulus such as heat being applied to the cell, has not yet been sufficiently elucidated. If a specific inhibitor is discovered, because of its mechanism it is expected to have a potential to be a new type drug. For example, it is known that a cell acquires a resistance to heat for a certain period of time after a thermotherapy for cancer. This is called acquisition of heat resistance. Since it takes 4–5 days for the heat resistance to disappear, a thermotherapy is typically conducted with a frequency of once or twice per week. It is expected that, if the acquisition of heat resistance can be disabled, the effect of cancer thermotherapy can be improved because it will then be possible to increase the number of times the therapy can be conducted. Moreover, it is clinically widely recognized that the effect of thermotherapy for cancer is greater when it is performed in combination with radiotherapy, chemotherapy, or the like, than when it is performed alone. For the mechanism of acquiring the heat resistance, it is believed that, for example, a protein which has been or is being denatured, is recovered by the action of HSP inducibly produced in a cell by heat, thereby reducing the cell killing effect. However, the details are still unclear. It is believed that HSP prevents apoptosis in a cancer cell. Therefore, it is possible, by suppressing the expression and induction of HSP, to cause normal apoptosis in a cancer cell, thereby controlling immortality or infinite proliferation of the cancer cell.

In the modern world, there has been an increasing number of cases of stress diseases caused by mental stress, including, for example, depression and anxiety. Many of the conventional drugs therefor have not been satisfactory in terms of their effectiveness and side effects. Moreover, the conventional drugs take a long time before they exhibit their effects, and the mechanism of action cannot be explained only with the receptor theory. Under such circumstances, a drug which selectively inhibit reuptake of serotonin has attracted attention as an antidepressant with reduced side effects. On the other hand, a serotonin (5-HT) receptor agonist has also attracted attention as an antianxiety drug. Some of these drugs (e.g., tandospirone citrate) provide both an antidepression action and an antianxiety action. This suggests that depression and anxiety, as stress diseases, are controlled at least partially by a common mechanism. It is expected that the essential characteristics of stress diseases such as depression and anxiety are elucidated, and a new drug are then developed based on a novel action mechanism. One strategy therefor is to associate the cellular-level stress with the animal-level stress from a novel point of view. The present inventors assumed that a drug which is capable of inhibiting activation of a heat shock factor at cellular level, would have an effect on stress diseases such as depression and anxiety at an animal level. Stress and a response thereto have a fundamental structure which is common among hierarchically different levels, i.e., the cell and the animal (Ichiro YAHARA, Stress Protein (ed., Kazuhiro NAGATA) pp. 257–262, 1994). This is supported by following: it is recognized that a stress response is purposive in that exposure to a stress make an animal or cell resistant to the next stress; a stress resistance is similarly obtained through different types of stress; stress is normally transient in an animal or cell, and the like. In view of these characteristics of stress, the present invention aims to treat a disease by controlling an overreaction or uncontrolled reaction in the individual cells, thereby restoring it to a normal state. The inhibition of signal transmission of the heat shock factor activation may be believed to inhibit the stress reaction of a cell and to place the cell in a stress-free state. Therefore, the suppression of stress reaction at a cellular-level through suppression of the HSF activation or the HSP expression can lead to suppression of stress reaction at an animal-level, whereby the inhibition of HSF activity or HSP expression can result in treatment or prevention of stress diseases such as depression and anxiety.

Currently, flavonoids such as quercetin is believed to have suppressive action on the HSP production, and to inhibit the activation of HSF by suppressing the expression of its mRNA. However, the mechanism of the action has not completely been known. Quercetin does not have a sufficient inhibitory effect on the HSF activity for use as a therapeutic. Moreover, there is fear of quercetin exhibiting potential side effects since it has various other physiological activities such as mutagenicity, an antivirus activity, a tyrosine kinase inhibiting activity, a protein kinase C inhibiting activity, and a lactate transport inhibiting activity.

Therefore, it has been desired for a drug to be developed which acts on the HSF activation more specifically so as to have a stronger effect and reduced side effects.

DISCLOSURE OF THE INVENTION

The present inventors have conducted extensive research in view of the above-described circumstances. As a result, the present inventors have discovered a drug which is effective in inhibiting the acquisition by a cell of heat resistance, such as that occurring in thermotherapy for cancer, through the inhibitory action on the activity of HSF as a transcription regulatory factor. Moreover, the present inventors have found, as the HSF activity inhibitor showed an antidepression action, etc., that it is also effective for stress diseases at animal level as well as cellular-level stress, thereby completing the present invention.

According to the first aspect, the present invention relates to a compound represented by general formula (I):

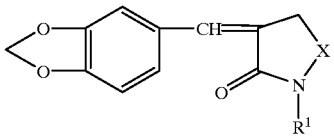

wherein X is —$CH_2$— and $R^1$ is $C_1$-$C_2$ alkyl, formyl or halogen; or X is —$(CH_2)_2$— and $R^1$ is $C_1$-$C_3$ alkyl, formyl, acetyl, hydrogen or halogen. In general formula (I), the olefinic double bond may take either an E-configuration or a Z-configuration.

In a preferred embodiment, the present invention relates to a compound wherein X is —$CH_2$— and $R^1$ is formyl.

In another preferred embodiment, the present invention relates to a compound wherein X is —$(CH_2)_2$— and $R^1$ is hydrogen.

In still another preferred embodiment, the present invention relates to a compound wherein X is —$(CH_2)_2$— and $R^1$ is formyl.

According to the second aspect, the present invention relates to an inhibitor of heat shock factor activity comprising, as an active ingredient thereof, a compound represented by general formula (I):

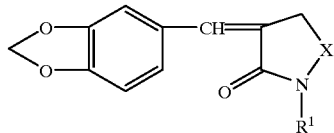

wherein X is —$CH_2$— and $R^1$ is $C_1$-$C_2$ alkyl, formyl, acetyl, hydrogen or halogen; or X is —$(CH_2)_2$— and $R^1$ is $C_1$-$C_3$ alkyl, formyl, acetyl, hydrogen or halogen.

In a preferred embodiment, the heat shock factor is HSF1.

In a preferred embodiment, the active ingredient is represented by general formula (I) wherein X is —$CH_2$— and $R^1$ is formyl.

In another preferred embodiment, the active ingredient is represented by general formula (I) wherein X is —$(CH_2)_2$— and $R^1$ is hydrogen.

In still another preferred embodiment, the active ingredient is represented by general formula (I) wherein X is —$CH_2$— and $R^1$ is hydrogen.

In still another preferred embodiment, the active ingredient is represented by general formula (I) wherein X is —$CH_2$— and $R^1$ is acetyl.

According to the third aspect, the present invention relates to an expression suppressor for a substance encoded by a structural gene having a heat shock element sequence in the gene region for transcriptional regulation, the suppressor comprising, as an active ingredient thereof, a compound represented by general formula (I):

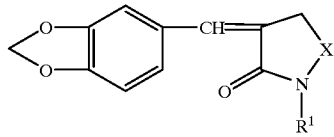

wherein X is —$CH_2$— and $R^1$ is $C_1$-$C_2$ alkyl, formyl, acetyl, hydrogen or halogen; or X is —$(CH_2)_2$— and $R^1$ is $C_1$-$C_3$ alkyl, formyl, acetyl, hydrogen or halogen.

In a preferred embodiment, the substance encoded by the structural gene having the heat shock element sequence in the gene region for transcriptional regulation is selected from the group consisting of HSP40, HSP47, HSP70, HSP90, HSP100, IL-1, α-fetoprotein, IFN-α, vitellogenin, and P-glycoprotein.

According to the fourth aspect, the present invention relates to a drug for treating or preventing a disease for which an inhibitory action on heat shock factor activity, or a suppressing action on the expression of a substance encoded by a structural gene having a heat shock element sequence in the gene region for transcriptional regulation is effective, the drug comprising, as an active ingredient thereof, a compound represented by general formula (I):

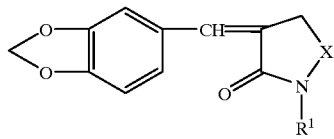

wherein X is —$CH_2$— and $R^1$ is $C_1$-$C_2$ alkyl, formyl, acetyl, hydrogen or halogen; or X is —$(CH_2)_2$— and $R^1$ is $C_1$-$C_3$ alkyl, formyl, acetyl, hydrogen or halogen.

In a preferred embodiment, the disease for which an inhibitory action on heat shock factor activity, or the suppression action on the expression of the substance encoded by the structural gene having the heat shock element sequence in the gene region for transcriptional regulation is effective is cancer.

According to a more preferred embodiment, in general formula (I), X is —CH$_2$— and R$^1$ is formyl.

In another preferred embodiment, the disease for which an inhibitory action on heat shock factor activity, or the suppressing action on the expression of the substance encoded by the structural gene having the heat shock element sequence in the gene region for transcriptional regulation is effective is a stress disease.

In a more preferred embodiment, the stress disease is depression.

According to a preferred embodiment, in general formula (I), X is —(CH$_2$)$_2$— and R$^1$ is hydrogen, or X is —CH$_2$— and R$^1$ is hydrogen.

According to the fifth aspect, the present invention relates to a drug for treating or preventing a stress disease which exhibits an inhibitory action on heat shock factor activity, or a suppressing action on the expression of a substance encoded by a structural gene having a heat shock element sequence in the gene region for transcriptional regulation.

BEST MODE FOR CARRYING OUT THE INVENTION

The present invention relates to a novel compound represented by general formula (I):

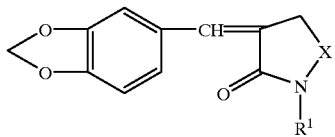

wherein X is —CH$_2$— and R$^1$ is C$_1$–C$_2$ alkyl, formyl or halogen; or X is —(CH$_2$)$_2$— and R$^1$ is C$_1$–C$_3$ alkyl, formyl, acetyl, hydrogen or halogen.

In general formula (I), the olefinic double bond may take either an E-configuration or a Z-configuration.

A preferred embodiment of the present invention is a compound represented by structural formula (I):

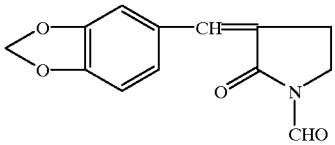

wherein X is —C$_2$— and R$^1$ is formyl.

Another preferred embodiment of the present invention is a compound represented by structural formula (II):

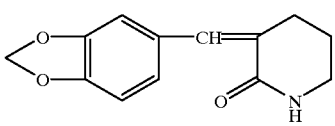

wherein X is —(CH$_2$)$_2$— and R$^1$ is hydrogen.

Regarding a method for producing a compound of the present invention represented by general formula (I):

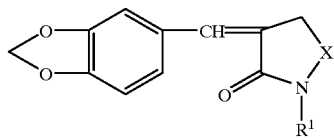

wherein X is —CH$_2$— and R$^1$ is C$_1$–C$_2$ alkyl, formyl, acetyl, hydrogen or halogen; or X is —(CH$_2$)$_2$— and R$^1$ is C$_1$–C$_3$ alkyl, formyl, acetyl, hydrogen or halogen, the compound can be obtained by reacting piperanol as shown below:

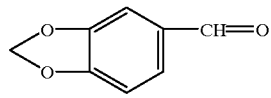

with a compound represented by general formula (II):

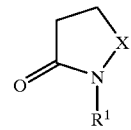

wherein X is —CH$_2$— and R$^1$ is C$_1$–C$_2$ alkyl, formyl, acetyl, hydrogen or halogen; or X is —(CH$_2$)$_2$— and R$^1$ is C$_1$–C$_3$ alkyl, formyl, acetyl, hydrogen or halogen, in the presence of a basic catalyst (e.g., an alkaline metal hydride such as sodium hydride or potassium hydride, an alkaline metal alcoholate such as sodium methylate or sodium ethylate, an alkaline metal amide such as lithium diisopropylamide, an organic acid salt such as sodium acetate, an alkaline metal carbonate such as sodium carbonate or potassium carbonate, an alkaline metal hydroxide such as sodium hydroxide, an organic acid base such as piperidine, etc.).

Alternatively, the compound can be obtained by reacting a compound represented by general formula (III):

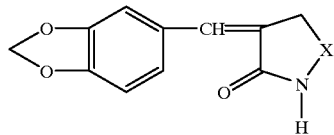

wherein X is —CH$_2$— and R$^1$ is C$_1$–C$_2$ alkyl, formyl, acetyl, hydrogen or halogen; or X is —(CH$_2$)$_2$— and R$^1$ is C$_1$–C$_3$ alkyl, formyl, acetyl, hydrogen or halogen, with a halogeno alkane such as iodomethane, an organic acid such as formic acid, an organic acid halide such as acetyl chloride, or a halogen such as chlorine, through a condensation reaction such as dehydrogenation condensation, or dehydrohalogenation condensation.

The present invention provides an inhibitor of heat shock factor activity, an expression suppressor for a substance encoded by a structural gene having a heat shock element sequence in the gene region for transcriptional regulation, or a drug for treating or preventing a disease for which an inhibitory action on heat shock factor activity or a suppressing action on the expression of a substance encoded by a structural gene having a heat shock element sequence in the gene region for transcriptional regulation is effective, the inhibitor or the suppressor comprising, as an active ingredient thereof, a compound represented by general formula (I):

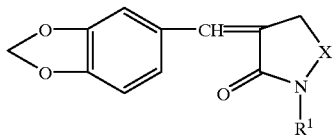

wherein X is —CH$_2$— and R$^1$ is C$_1$–C$_2$ alkyl, formyl, acetyl, hydrogen or halogen; or X is —(CH$_2$)$_2$— and R$^1$ is C$_1$–C$_3$ alkyl, formyl, acetyl, hydrogen or halogen. The active ingredient can inhibit the activity of the transcriptional control factor HSF, thereby inhibiting induction of the transcription of a structural gene having a DNA sequence recognized by HSF (i.e., HSE) in the gene region for transcriptional regulation. Thus, the active ingredient specifically suppresses a protein induced/expressed by unusual stress such as heat while not inhibiting the basic expression of molecular species which are essential for the cell. Therefore, the active ingredient is capable of effectively inhibiting and suppressing a protein which is encoded by a structural gene having HSE in the gene region for transcriptional regulation and which is induced/expressed by stress such as heat.

For typical stress proteins including a small molecular HSP such as HSP27 or HSP47, an HSP60 family, an HSP70 family, an HSP90 family and an HSP100 family, a certain type of enzymes involved in saccharometabolism, IL-1, α-fetoprotein, IFN-α, vitellogenin, P-glycoprotein, or the like, for example, an HSE sequence recognized by HSF is present in the promoter sequence for the coded gene. Therefore, it is believed that suppressing the induction of the gene expression from such genes can result in preventing/treating diseases related to the genes. Therefore, a compound which exhibits inhibitory action on the heat shock factor activity or a suppressing action on the expression of a substance encoded by a structural gene having a heat shock element sequence in the gene region for transcriptional regulation is effective in treating and preventing, for example, cancer and a disease, such as depression or anxiety, which is considered to be caused by stress. Therapies for cancer include thermotherapy for cancer alone, thermotherapy for cancer in combination with radiotherapy or a chemotherapeutic, and resistance-overcoming therapy wherein the resistance acquired by a cancer cell is overcome through the inhibition of multidrug resistance acquisition, thereby recovering the effect of a chemotherapeutic on the cancer cell.

The inventive inhibitor of heat shock factor activity, or the inventive suppressor of the expression of a substance encoded by a structural gene having a heat shock element sequence in the gene region for transcriptional regulation, improves the therapeutic effect of thermotherapy for cancer based on its suppressing action on cellular heat resistance. The dosage of the compound of the prevent invention for a human in thermotherapy for cancer can be determined by a method known in the art. For example, the dosage for a human can be determined as a value equivalent to the dosage suitable for a mouse which is determined by a test as described in Example 8. The dosage for a mouse is typically in the range of 0.01 to 2000 mg/kg, preferably 0.1 to 1000 mg/kg, more preferably 1 to 500 mg/kg.

The inventive inhibitor of heat shock factor activity or the inventive suppressor of expression of a substance encoded by a structural gene having a heat shock element sequence in the gene region for transcriptional regulation, also exhibit an antidepression action. The dosage of the compound of the present invention as an antidepressant can be determined by a method well known in the art. For example, the dosage for a human can be determined as a value equivalent to the dosage suitable for a mouse which is determined by a test as described in Example 7. The dosage for a mouse is typically in the range of 0.1 to 5000 mg/kg, preferably 1 to 2000 mg/kg, more preferably 10 to 500 mg/kg. Other depression models from which an appropriate dosage can be derived include a forced swimming test as described in Example 7 as well as a stress (chronic stress) model, a muricide model, a reserpine antagonizing model, an electrically self-stimulation model (Psychopharmacology, 83: 1, 1984), a tail suspension model (Jpn. J. Phychopharmacol., 12: 207, 1992).

The effect on other stress diseases of the inventive inhibitor of the heat shock factor activity or the inventive suppressor of the expression of a substance encoded by a structural gene having a heat shock element sequence in the gene region for transcriptional regulation can be confirmed by pharmacological or behavioral pharmacological experiments that are well known in the art. For the antianxiety action, for example, a conflict model (Jpn. J. Psychopharmacol., 15: 115, 1995), an elevated plus maze method (Jpn. J. Psychopharmacol., 15: 125, 1995), a mental stress loading method (Jpn. J. Psychopharmacol., 15: 375, 1995), and the like, may be used. Experimental methods for other stress diseases are described in detail in, for example, "Doubutsu moderu riyo shusei [Collection of Animal Model Usage]" (Ryuta ITO, et al. eds., R&D Planning, 1985). The dosage of the compound of the present invention for a human can be determined by a method well known in the art. For example, the dosage for a human can be extrapolated from the effective dosage determined in the above-described animal experiments by using a method well known in the art.

The actual dosage is adjusted by a clinician according to the need of a particular patient.

The inventive inhibitor of the heat shock factor activity or the inventive suppressor of the expression of a substance encoded by a structural gene having a heat shock element sequence in the gene region for transcriptional regulation, or a drug comprising the same for treating or preventing cancer or stress diseases can be administered orally, anterally or parenterally. Specific types of formulation include, for example, an oral formulation such as tablet, powder, capsule, granule, fine granule or syrup, a parenteral formulation such as suppository, ointment, injection, cream for topical application or eye drop.

The inventive inhibitor of the heat shock factor activity or the inventive suppressor of the expression of a substance encoded by a structural gene having a heat shock element sequence in the gene region for transcriptional regulation, a drug comprising the same for treating or preventing cancer or a drug comprising the same for treating or preventing stress diseases can be formulated with a carrier which may optionally comprise any organic or inorganic, solid or liquid component suitable for oral, enteral or parenteral administration. For example, such as optional component may be a excipient such as crystalline cellulose, gelatin, lactose, saccharose, starch, corn starch, dextrin, mannite, magnesium stearate, talc, vegetable and animal fats, oil, gum, polyalkylene glycol, Arabian gum or pectin, a binder, a disintegrator, a lubricant, a flavor, a filler, a coloring agent, a stabilizer, an isotonic agent, a solubilizer, a dispersant, a solubilizing agent, an emulsifier, a coloring agent, a wetting agent, and an antioxidant. The compound of the present invention can be included in the formulation at 0.001 to 100%. Any other compatible inhibitor or drug may further be included. In such a case, the compound of the present invention is not necessarily the main component of the formulation.

Although he present invention will now be described in greater detail by way of examples, it is not limited to those examples.

The compound of the present invention can be synthesized as follows.

EXAMPLE 1

Synthesis of Compounds 101 and 102

A solution of N-acetyl-2-pyrrolidone (70.0 g, 0.55 mol) and piperonal (82.0 g, 0.55 mol) in tetrahydrofuran (500 ml) was dropped into a suspension of sodium hydride (60% mineral oil suspension, 63.0 g, 1:57 mol) in tetrahydrofuran (1000 ml) while cooling on ice under an argon atmosphere, after which the reaction solution was stirred overnight at room temperature. The reaction solution was neutralized with dilute sulfuric acid, extracted with chloroform, washed with saturated saline, dried with sodium sulphate, and filtered, and then the solvent was distilled away under vacuum. The resultant reaction product was re-crystallized with 2-propanol, thereby obtaining Compound 101 (79.0 g, yield 65%).

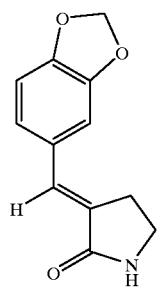

Compound 101

NMR (400 MHz, CDCl$_3$) 3.03 (2H, m), 3.48 (2H, m), 6.03 (2H, s), 6.29 (1H, s), 6.86 (1H, d), 7.24 (1H, s), 7.49 (1H, d)

A solution of Compound 101 (82.0 g, 380 mmol) in formic acid (500 ml) was heat refluxed for 20 hours by using a Dean-Stark azeotropic apparatus. The solvent was distilled away under vacuum, after which the residue was separated by silica gel column chromatography (eluate: chloroform-:ethyl acetate=1:1), and re-crystallized with chloroform, thereby obtaining Compound 102 (10.5 g, yield: 11%).

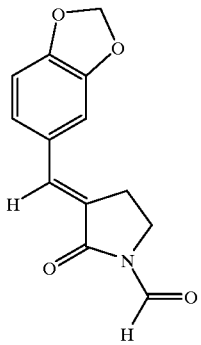

Compound 102

NMR (400 MHz, CDCl$_3$) 3.10 (2H, m), 3.84 (2H, m), 6.05 (2H, s), 6.89 (1H, d), 7.01 (1H, s), 7.07 (1H, d), 7.55 (1H, s), 9.25 (1H, s)

EXAMPLE 2

Synthesis of Compounds 103 and 104

Compound 103 was obtained through a procedure similar to that used for Compound 101, while using N-acetyl-2-piperidone (77.5 g, 0.55 mol) and piperonal (82.0 g, 0.55 mol) as materials.

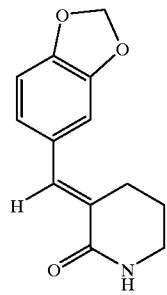

Compound 103

Compound 104 was obtained through a procedure similar to that used for Compound 102, while using Compound 103 (97.5 g, 380 mmol) as a material.

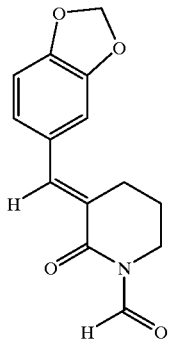

Compound 104

EXAMPLE 3

Expression Suppression Experiment Using Reporter Protein

A plasmid was produced in which a β-galactosidase gene was located downstream of a promoter region including the HSE sequence for HSP47. Chinese hamster ovary (CHO) cells were transfected with the plasmid to obtain stable transformant A. On the other hand, another plasmid was produced in which a β-galactosidase gene was located downstream of an SV40 clearly promoter which does not include the HSE sequence but has many other transcriptional factor control regions. Chinese hamster overy (CHO) cells were transfected with the plasmid to obtain stable transformant B. These stable transformants were pre-treated with Compounds 101, 102 and 103 above and Compound C (1-acetyl-3-benzo-(1,3)dioxole-5-ylmethylene-pyrrolidin-2-one; this compound is represented by general formula (I) of the present invention wherein X is —$CH_2$— and $R^1$ is acetyl) in a $CO_2$ incubator at 37° C. for 60 min. Then, the transformants were subjected to a heat shock of 42° C. for 90 min, recovered at 37° C. for 2 hours, and incubated at a room temperature for 30 min with 4-methylumbelliferyl-β-D-galactoside as a substance for the activity of β-galactosidase expressed in the cell. Then, the fluorescence was measured (excitation at 365 nm, emission at 450 nm). The amount of β-galactosidase expressed after a treatment with test compounds or the known HSF and HSP inhibitor quercetin as a control agent was divided by the amount of β-galactosidase expressed after a treatment with dimethylsulfoxide (DMSO) as a solvent control, thereby calculating the expression rate (%) as shown in Table 1.

TABLE 1

| Compounds | Conc. | Expression Rate (%) | |
|---|---|---|---|
| | | Transformant A | Transformant B |
| DMSO | 0.25% | 100 | 100 |
| Quercetin | 5 μM | 99 | 96 |
| | 50 μM | 25 | 82 |
| | 100 μM | 6 | 58 |
| Compound 101 | 5 μM | 46 | 90 |
| | 50 μM | 1 | 61 |
| Compound 102 | 5 μM | 57 | 88 |
| | 50 μM | 3 | 75 |
| | 100 μM | 0 | 69 |
| Compound 103 | 5 μM | 47 | 93 |
| | 50 μM | 10 | 62 |
| | 100 μM | 2 | 46 |
| Compound C | 5 μM | 40 | 91 |
| | 50 μM | 11 | 88 |

Quercetin, which has been confirmed as an HSF inhibitor and an HSP inhibitor, was used as a positive control. The treatment with the compounds of the present invention clearly suppressed the expression of β-galactosidase, a reporter protein, at the transcription level, showing an effect greater than that obtained with the known inhibitor quercetin.

EXAMPLE 4

Transcription Suppression of HSP70 (Inducible Type) mRNA by Northern Hybridization Method COLO320DM cells (ATCC CCL-220) were pre-treated with Compounds 101, 102 and 103 in a $CO_2$ incubator at 37° C. for 60 min using 10% FCS, DMEM medium (Gibco BRL), after which the cell was subjected to a heat shock of 42° C. for 90 min. Immediately thereafter, the treated cells were collected, and total RNA was extracted from the cells by using the acid guanidine thiocyanate phenol chloroform (AGPC) method. The total RNA was electrophoresed, transferred to a nylon filter, and the amounts of HSP mRNA were compared among experimental groups by using the Northern hybridization method. cDNA of HSP70 (inducible type) labeled with [α-$^{32}$P] dCTP was used as a probe, and cDNA of β-actin was used as an internal control. The treatment with Compounds 101, 102 and 103 specifically and significantly suppressed the mRMA transcription of HSP70, exhibiting an inhibitory effect at the transcription level. Table 2 provides comparison in the amount of transcription of HSP70 (inducible type) among cells which were subjected to a heat shock after treatment with the respective compounds, with the amount of induced transcription in a cell treated with the control solvent DMSO being 1.0.

TABLE 2

| Compounds | | Transcription Amount of HSP70 (induced type) |
|---|---|---|
| DMSO | (0.25%) | 1.0 |
| Quercetin | (100 μM) | 0.4 |
| Compound 101 | (100 μM) | 0.03 |
| Compound 102 | (100 μM) | 0.04 |
| Compound 103 | (100 μM) | 0.1 |

No substantial change in the amount of β-actin was observed among the treatments. For cells which were not subjected to a heat shock, substantially no HSP70 (inducible type) mRNA transcription was observed.

EXAMPLE 5

HSP Expression Induction Suppression by 2-Dimensional Electrophoresis

COLO320DM cells were pre-treated with Compounds 101, 102 and 103 at 37° C. for 60 min, followed by application of a heat shock at 42° C. for 90 min, and recovery at 37° C. for 2 hours. Then, the media were replaced with methionine-free media, and the cells were treated at 37° C. for 1 hour with $^{32}$S-methionine to label newly synthesized proteins.

The cell lysate was obtained, subjected to an isoelectric focusing as the first dimension and then to an expansion by SDS-PAGE as the second dimension. Then, the gel was subjected to fluorography so as to compare between the amounts of HSP synthesized with and without heat induction. Comparison between the amounts of β-actin synthesized as an internal control with and without heat induction confirmed that the other proteins were normally synthesized. Table 3 provides a comparison in the HSP heat induction by a heat shock between experimental groups with the DMSO solvent control group in which the HSP synthesis was strongly induced.

TABLE 3

| | HSP Induction by Heat Shock Treatment | | | | | |
|---|---|---|---|---|---|---|
| Compounds | HPS40 | HSP47 | HSP70 | HSP90 | HSP100 | β-actin |
| DMSO (0.25%) | ↑↑↑ | ↑↑↑ | ↑↑↑ | ↑↑↑ | ↑↑↑ | no change |
| Quercetin (100 μM) | ↓↓ | ↓↓ | ↓ | ↓ | ↓ | no change |
| Compound 101 (100 μM) | ↓↓↓ | ↓↓↓ | ↓↓↓ | ↓↓↓ | ↓↓↓ | no change |
| Compound 102 (100 μM) | ↓↓↓ | ↓↓↓ | ↓↓↓ | ↓↓↓ | ↓↓↓ | no change |
| Compound 103 (100 μM) | ↓↓↓ | ↓↓↓ | ↓↓↓ | ↓↓↓ | ↓↓↓ | no change |

↑↑↑: Not Suppressed (Strongly Induced);
↓: Slightly Suppressed;
↓↓: Suppressed;
↓↓↓: Strongly Suppressed The amount of β-actin synthesized did not substantially vary among the heat shock group, the non-heat shock group and sample treated groups. The treatment with the compounds of the present invention clearly suppressed the protein synthesis of all HSPs specifically under expression induction conditions, exhibiting much greater effect than that with the known inhibitor quercetin.

EXAMPLE 6

Cell Heat Resistance Suppression Action

COLO320DM cells were pre-treated with the above-described compounds at 37° C. for 60 min, followed by pre-heating by application of a heat shock of 42° C. for 90 min. The cells were further treated at 37° C. for 60 min. Then, the media were replaced respectively with compound-free media, and the cells were further incubated at 37° C. for 60 min. Thereafter, the cells were treated at 45° C. for 60 min, and cultured for about 10 days followed by measurement of the number of surviving cells as the number of colonies using a colony formation assay. Note, however, that the colonies formed for Compounds 101, 102 and 103 were counted despite being significantly smaller colonies than those formed after the treatment with a DMSO solvent. If those colonies with a diameter of about 0.5 mm or less had been ignored as in a normal evaluation, an even greater heat resistance inhibiting effect would have been exhibited, whereby the surviving fraction would have lowered by 2–3 orders or magnitude (i.e., 0.001%–0.01%). The number of colonies formed without the treatment at 45° C. was substantially the same among all of the drugs. The results are shown in Table 4.

TABLE 4

| Compounds | Surviving Fraction (%) |
|---|---|
| DMSO (0.25%) | 18 |
| Quercetin (100 μM) | 6 |
| Compound 101 (100 μM) | <1 |
| Compound 102 (100 μM) | <1 |
| Compound 103 (100 μM) | <1 |

The compounds of the present invention clearly confirmed to have the inhibitory effect on the acquisition of cell heat resistance, which is greater than that obtained with the known inhibitor quercetin. The surviving fraction was calculated according to the following formula:

Surviving Fraction (%)=A/B×100
A: Cell Survival Fraction With Treatment at 45° C. for 60 min
B: Cell Survival Fraction Without Treatment at 45° C.
Cell Survival Fraction=C/D
C: Number of Surviving Cells
D: Number of Cells Seeded

EXAMPLE 7

Antidepressant Effect in Forced Swimming Test with Rats

The experiment was conducted as a partial modification of the Porsolt, R. D. et al. method (Eur. J. Pharm., 47: 379, 1978). In particular, a Wistar male rat (5 weeks of age, weight: 130–150 g) was dropped into water (temperature: 25° C.) about 15 cm deep in a glass cylinder having an inner diameter of 18 cm and a height of 40 cm. The rat was taken out after 15 min, dried and put back into a home cage. After 24 hours, the rat was dropped again into water in the same cylinder, and periods of no movement (periods of time during which the rat did not move) during a period of 5 minutes were accumulated by using a stopwatch (a 5-minute test). One hundred mg/kg of each test compound, suspended in a physiological saline, was orally administered once before the 5-minute test so as to examine the antidepression effect. One hundred mg/kg of imipramine, a known antidepressant, as a control drug and 5 ml/kg of a physiological saline as a control were similarly orally administered. A shortened no-movement period was calculated as a suppression rate according to the following formula:

Suppression Rate (%)=(E−F)/E×100
E: No-Movement Period with Physiological Saline
F: No-Movement Period with Test Compound
The results are shown in Table 5.

TABLE 5

| Compounds | Dosage (mg/kg) | No-Movement Period (sec) | Suppression Rate (%) |
|---|---|---|---|
| Saline | — | 205 | 0 |
| Compound 101 | 100 | 145 | 29 |
| Compound 103 | 100 | 90 | 56 |
| Imipramine | 100 | 180 | 12 |

The administration of the compound of the present invention clearly shortened the no-movement period, exhibiting an effect greater than that obtained with the known antidepressant imipramine.

EXAMPLE 8

Inhibitory Effect on Cancer Heat Resistance Acquisition Using Mice with Cancer

A murine carcinoma cell (SCC VII) was implanted in the right leg of C3H/He mice (male, about 10 mice for each group), and the experiment was started when the tumor became about 1 cm in diameter. The tumor was heated by soaking the tumor site of each mouse under general anaesthesia into a constant temperature bath at 44° C. The inhibitory effect on the heat resistance acquisition by cancer cell was examined by a growth delay assay on the tumor. Two hundred mg/kg of each test compound, suspended in an olive oil, was intraperitoneally administered once 6 hours before the first heating. The first heating was performed for 10 minutes (H1), and the second heating was performed for 30 minutes (H2), with a recovery period of 8 hours at room temperature between the first heating and the second heating.

TABLE 6

| Groups | Means days before tumor tripled |
| --- | --- |
| No Treatment | 8.3 |
| Compound 102 | 8.4 |
| (H1)8 hr(H2) | 9.6 |
| (H1)8 hr(H2) + Compound 102 | 12.6 |
| 44° C., 30 min | 13.9 |
| 44° C., 30 min + Compound 102 | 13.3 |

The compounds of the present invention clearly confirmed to have the inhibitory effect on the heat resistance acquisition by a cancer cell.

INDUSTRIAL APPLICABILITY

The present invention provides an inhibitor of a heat shock factor (HSF, particularly HSF1) activity or an suppressor or protein production induction regulated by HSF. The present invention also provides a novel benzo-1,3-dioxole compound which is useful in treating or preventing cancer through thermotherapy and in treating or preventing stress diseases such as depression and anxiety. The present invention further provides a drug for preventing thermotherapy resistance and a drug for treating or preventing stress diseases, comprising, as an active ingredient thereof, a benzo-1,3-dioxole compound.

What is claimed is:

1. A compound selected from the formula (I):

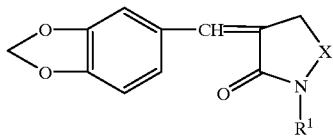

wherein X is —CH$_2$— and R$^1$ is C$_1$–C$_2$ alkyl, formyl or halogen; or X is —(CH$_2$)$_2$— and R$^1$ is C$_1$–C$_3$ alkyl, formyl, acetyl, hydrogen or halogen.

2. The compound according to claim 1, wherein X is —CH$_2$— and R$^1$ is formyl.

3. The compound according to claim 1, wherein X is —(CH$_2$)$_2$— and R$^1$ is hydrogen.

4. The compound according to claim 1, wherein X is —(CH$_2$)$_2$— and R$^1$ is formyl.

5. The compound of claim 1, wherein the olefinic double bond is in the E-configuration.

6. The compound of claim 1, wherein the olefinic double bond is in the Z-configuration.

7. A composition comprising a compound selected from the formula:

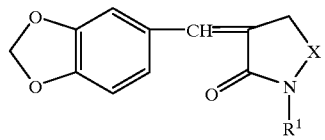

and a pharmaceutically acceptable carrier, wherein:
X is —CH$_2$— and R$^1$ is C$_1$–C$_2$ alkyl, formyl, or halogen; or
X is —(CH$_2$)$_2$— and R$^1$ is C$_1$–C$_3$ alkyl, formyl, acetyl, hydrogen, or halogen.

8. The composition of claim 7, wherein X is —CH$_2$— and R$^1$ is formyl.

9. The composition of claim 7, wherein X is —(CH$_2$)$_2$— and R$^1$ is hydrogen.

10. The composition of claim 7, wherein X is —(CH$_2$)$_2$— and R$^1$ is formyl.

11. The composition of claim 7, wherein the olefinic double bond is in the E-configuration.

12. The composition of claim 7, wherein the olefinic double bond is in the Z-configuration.

13. A method of inhibiting heat shock factor activation in cellular level stress; the method comprising contacting a cell with an effective amount of a compound selected from the formula:

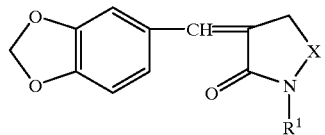

wherein:
X is —CH$_2$— and R$^1$ is C$_1$–C$_2$ alkyl, formyl, or halogen; or
X is —(CH$_2$)$_2$— R$^1$ is C$_1$–C$_3$ alkyl, formyl, acetyl, hydrogen, or halogen;
said stress induced heat shock factor activation is suppressed.

14. The method of claim 13, wherein X is —CH$_2$— and R$^1$ is formyl.

15. The method of claim 13, wherein X is —(CH$_2$)$_2$— and R$^1$ is hydrogen.

16. The method of claim 13, wherein X is —(CH$_2$)$_2$— and R$^1$ is formyl.

17. The method of claim 13, wherein the heat shock factor is HSF1.

18. The method of claim 13, wherein the olefinic double bond is in the E-configuration.

19. The method of claim 13, wherein the olefinic double bond is in the Z-configuration.

20. A method of treating a stress disease, the method comprising administering to an animal a heat shock factor inhibitory amount of a compound selected from the formula:

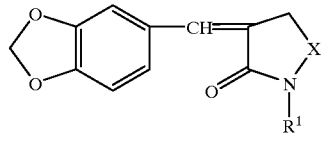

wherein:
X is —CH$_2$— and R$^1$ is C$_1$–C$_2$ alkyl, formyl, or halogen; or

X is —(CH$_2$)$_2$— and R$^1$ is C$_1$–C$_3$ alkyl, formyl, acetyl, hydrogen, or halogen.

21. The method of claim 20, wherein X is —CH$_2$— and R$^1$ is formyl.

22. The method of claim 20, wherein X is —(CH$_2$)$_2$— and R$^1$ is hydrogen.

23. The method of claim 20, wherein X is —(CH$_2$)$_2$— and R$^1$ is formyl.

24. The method of claim 20, wherein the olefinic double bond is in the E-configuration.

25. The method of claim 20, wherein the olefinic double bond is in the Z-configuration.

26. The method of claim 20, wherein the animal is a human.

27. A method of treating depression, the method comprising administering to an animal a heat shock factor inhibitory amount of a compound selected from the formula:

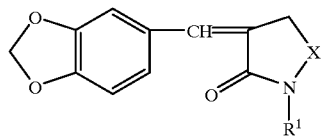

wherein:

X is —CH$_2$— and R$^1$ is C$_1$–C$_2$ alkyl, formyl, or halogen; or

X is —(CH$_2$)$_2$— and R$^1$ is C$_1$–C$_3$ alkyl, formyl, acetyl, hydrogen, or halogen.

28. The method of claim 27, wherein X is —CH$_2$— and R$^1$ is formyl.

29. The method of claim 27, wherein X is —(CH$_2$)$_2$— and R$^1$ is hydrogen.

30. The method of claim 27, wherein X is —(CH$_2$)$_2$— and R$^1$ is formyl.

31. The method of claim 27, wherein the olefinic double bond is in the E-configuration.

32. The method of claim 27, wherein the olefinic double bond is in the Z-configuration.

33. The method of claim 27, wherein the animal is a human.

* * * * *